United States Patent [19]

Giordani

[11] Patent Number: 5,131,389
[45] Date of Patent: Jul. 21, 1992

[54] ELECTROSTIMULATING DEVICE

[76] Inventor: Antonio I. Giordani, R.Cel.José Euzebio, 73-01239-S.Paulo, SP, Brazil

[21] Appl. No.: 444,168
[22] PCT Filed: Apr. 28, 1988
[86] PCT No.: PCT/BR88/00005
§ 371 Date: Sep. 20, 1989
§ 102(e) Date: Sep. 20, 1989
[87] PCT Pub. No.: WO89/06554
PCT Pub. Date: Jul. 27, 1989
[51] Int. Cl.⁵ .............................................. A61N 1/32
[52] U.S. Cl. .................................................... 128/422
[58] Field of Search ................ 128/420 R, 421, 422, 128/423 R

[56] References Cited

U.S. PATENT DOCUMENTS

| | | | |
|---|---|---|---|
| 3,886,931 | 6/1975 | Rodler | 128/420 R |
| 3,983,881 | 10/1976 | Wickham | 128/422 |
| 4,210,115 | 7/1980 | Keller, Jr. | 128/421 |
| 4,230,121 | 10/1980 | Stanton | 128/422 |
| 4,237,899 | 12/1980 | Hagfors et al. | 128/422 |
| 4,340,063 | 7/1982 | Maurer | 128/421 |
| 4,503,863 | 3/1985 | Katims | 128/42138,223 |
| 4,803,988 | 2/1989 | Thomson | 128/421 |
| 4,938,223 | 7/1990 | Charters et al. | 128/421 |

Primary Examiner—William E. Kamm
Attorney, Agent, or Firm—Baker & McKenzie

[57] ABSTRACT

A series of devices for medical, therapeutic and odontological treatments, which employ impulse-therapy or transcutaneous nervous electrostimulation as a means of physical, rational and non-invasive relaxation of specific muscle areas; the developed basic electrostimulating device consists of a triangular signal generator, followed by an amplifier, which is connected to a modulation controller. A squared signal generator is connected to a first stage conditioner which, in turn, is connected in parallel to a frequency divider, to a final amplifier, and to another second stage signal conditioner, and another final amplifier follows the latter. The referred frequency divider is also connected to a third stage signal conditioner through a key of three positions (A, B, C) which provides for varied frequency settings. A third stage signal conditioner is connected to a low frequency signal controller.

16 Claims, 6 Drawing Sheets

5,131,389

ELECTROSTIMULATING DEVICE

FIELD OF INVENTION

The present invention refers to an Electrostimulating Device for applications in medical and odontological fields.

More specifically, the invention deals with a series of devices for medical, therapeutic and odontological treatments, that employ impulse-therapy or transcutaneous nervous electrostimulation, also called "TENS", as means of physiological, rational and non-invasive relaxation of specific muscular areas.

BACKGROUND

Pain accompanies mankind from his birth until the end of his life. Perhaps for this reason, one type of fear, among many which exist, also accompanies man throughout his life, the fear of pain.

In odontological treatment, for example, fear of pain is almost constant, in spite of the fact that the advances in modern dentistry have been able to soothe in an extraordinary way the unpleasant sensations experienced by the patient. Tension and anxiety still remain and constitute factors that discourage many patients from going to the dentist, afraid of the pain they might feel. Fear is the most significant factor among the many reasons given for failure to see a dentist.

The search for solutions to diminish the "stress" of odontological patients has been a concern of dental care providers. The impulse-therapy or transcutaneous nervous electrostimulation, i.e. "ENT" or "TENS", is an efficient method to achieve a physiological, rational and non-invasive relaxation, of specific muscular areas.

In 1975, Bernard Jankelson initiated studies on its applications in the odontological area, and developed a device, the "Myo-Monitor" of specific use in dentistry. Since then, many similar devices have been developed with the same purpose of relaxation and regulation of the musculature of the odontostomatognatic system. All of them utilize low frequency, fixed or variable (from 40 to 350 impulses per minute) to attain the proposed objectives. These devices, in spite of presenting results considered satisfactory, have several restrictions, due, mainly, to the adoption of a unique band of performance of the electrostimulating signals, the most critical being the following:

The high frequency applied separately promotes a fast analgesic and relaxing effect, however of low duration after its application.

The low frequency applied separately promotes analgesic, relaxation of longer duration, after application; however, it takes longer for the effect to initiate and, besides this, it provokes an unpleasant sensation in the patient.

The low frequency can only be utilized up to 300 pulses per minute, for above this it promotes muscular stress, which is a totally undesirable effect.

SUMMARY OF THE INVENTION

The developed electrostimulating device presents technical innovations, which resulted from experiences and research carried out with other stimulating devices, which indicated that the incorporation of high frequency, modulated to high and low frequencies, isolated or superposed, improved appreciably the efficiency of the "TENS"·results, in the treatment of the symptomatology of pain and in the relaxation of muscles.

Thus, the following may be pointed out as the main innovations of the electrostimulating device:

Incorporation of the modulation of the low frequency pulses, in those of high frequency, in frequency as well as in phase. Under these conditions, the characteristics of the pulse length are kept stable and adjustments are allowed regardless of intensity;

Introduction of the modulation of the high frequency signal by another low frequency signal (in the range of 0.5 to 8.333 Hz), which wave may be triangular or sinusoidal. Internally, the modulation may be adjusted between 0 to 100%. Practical experiments indicated a modulation factor of 50% as being of good efficiency in the impulse-therapy applications, due to the remnant effect of the continuous low frequency signal; and combined utilization of the resources described above, which allows the therapeutic application of the three signals simultaneously.

Such innovations increase the field of application of the device, due to the combination of frequencies which it permits. Resulting from this, devices can be made for odontological, physiotherapeutic and therapeutic applications, constituting a series of stimulating devices.

In order to achieve the objectives of the invention, the electrostimulator consists of two generators of base time and associated circuits. One of the generators is destined to the generation of high and low frequency signals and the other, to the generation of the signal which constitutes the modulation.

The characteristic of the form of the output wave is of the squared alternating type with approximately squared forms on both the positive and negative directions, or squared in either the positive or negative direction with or without an exponential form in the other. Other possible forms of waves are: triangular, sinusoidal, double-phase or monophase type.

Each stimulus must have the pulse length adjustable from 60 to 20,000 microseconds and current limitation of a maximum of 50 milliamperes, and the signal that composes each stimulus may be of the unique type or the "burst" type.

BEST MODE FOR CARRYING OUT THE INVENTION

Figure 1:
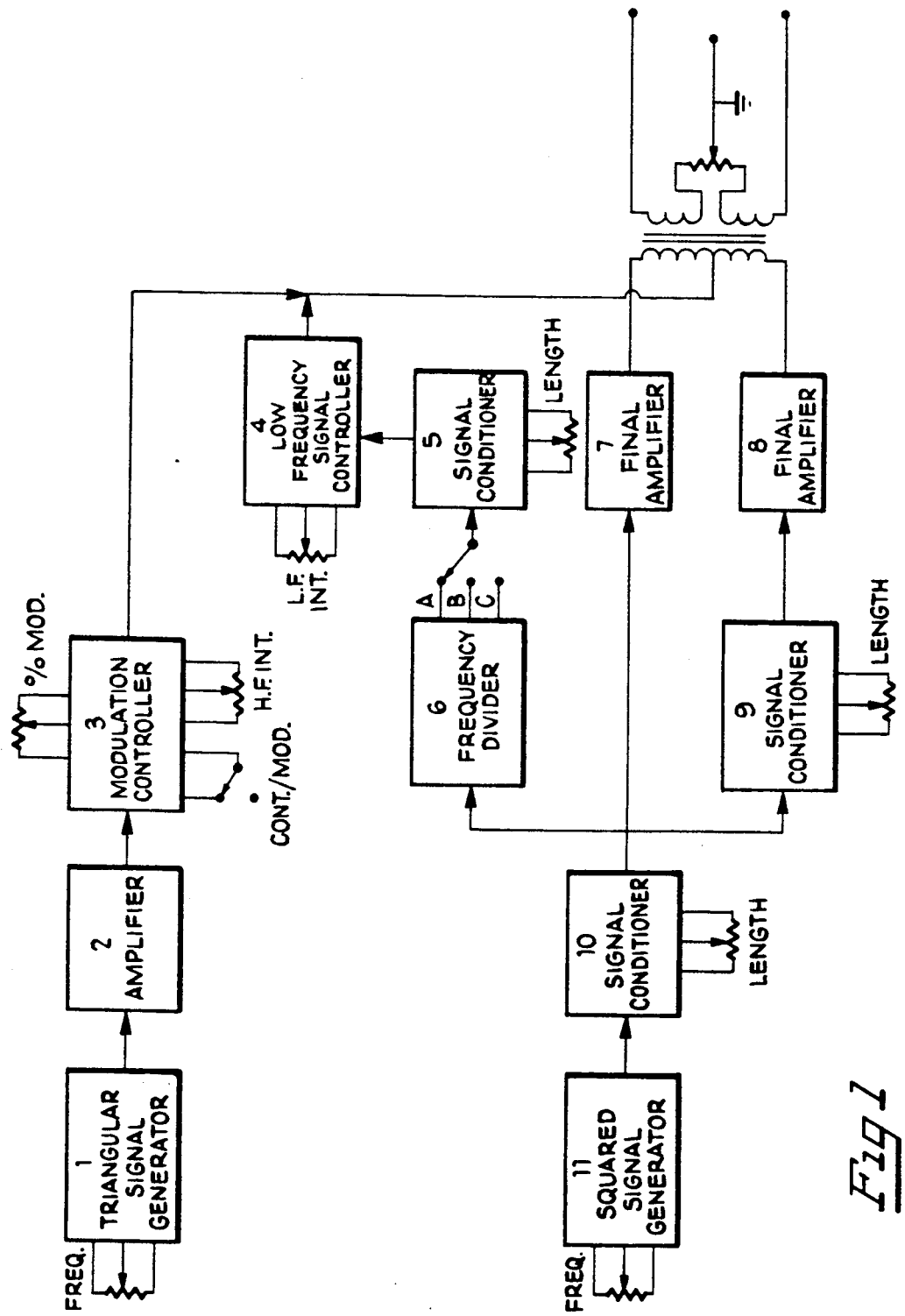
FIG. 1 is a block diagram representing the functional structure of the electrostimulating device for odontological applications, representing the basic units which constitute it.
Figure 2:
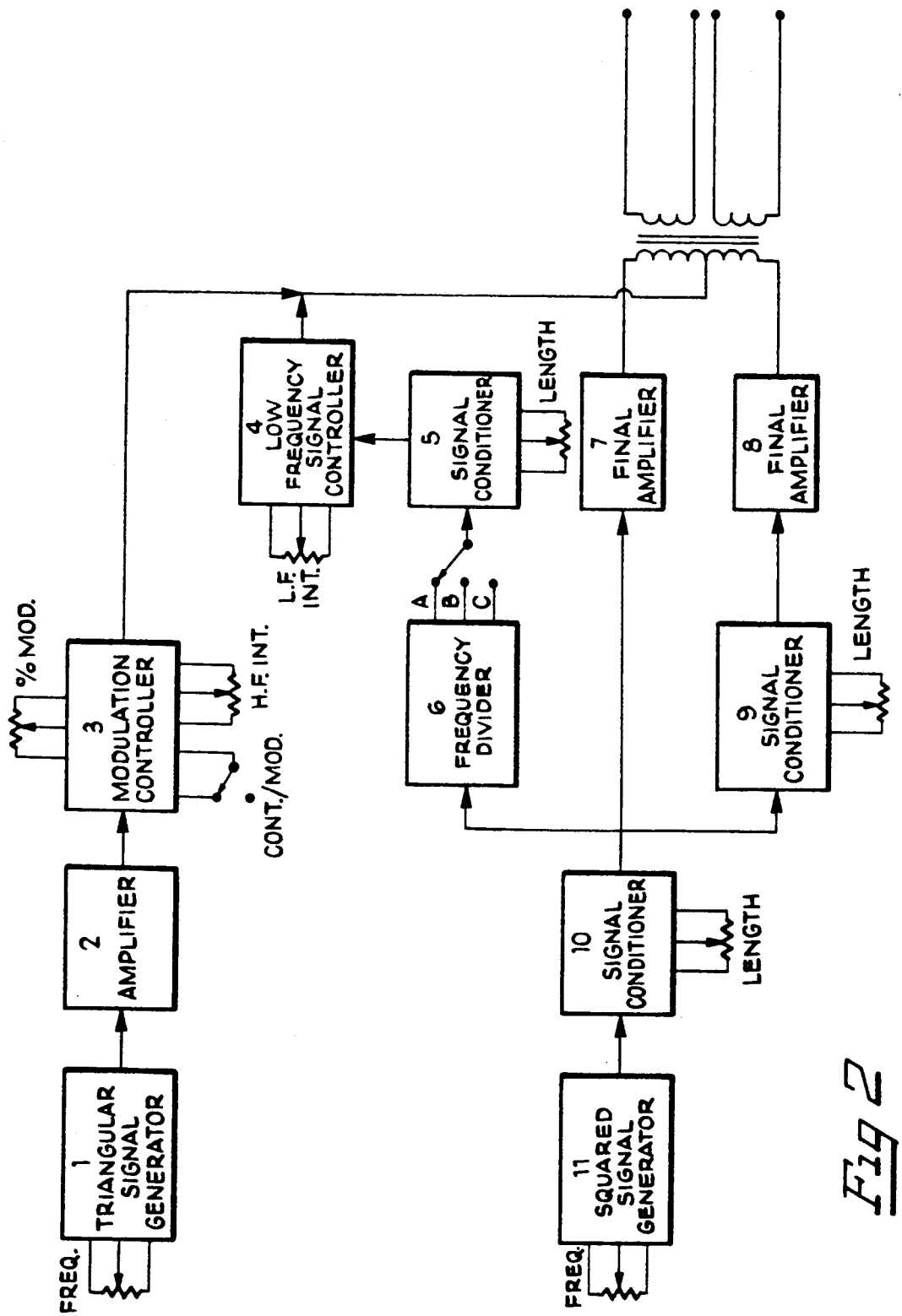
FIGS. 2, 3 and 4 are block diagrams representing the functional structures of different forms of the electrostimulating device, applied to other medical and odontological fields.
Figure 3:
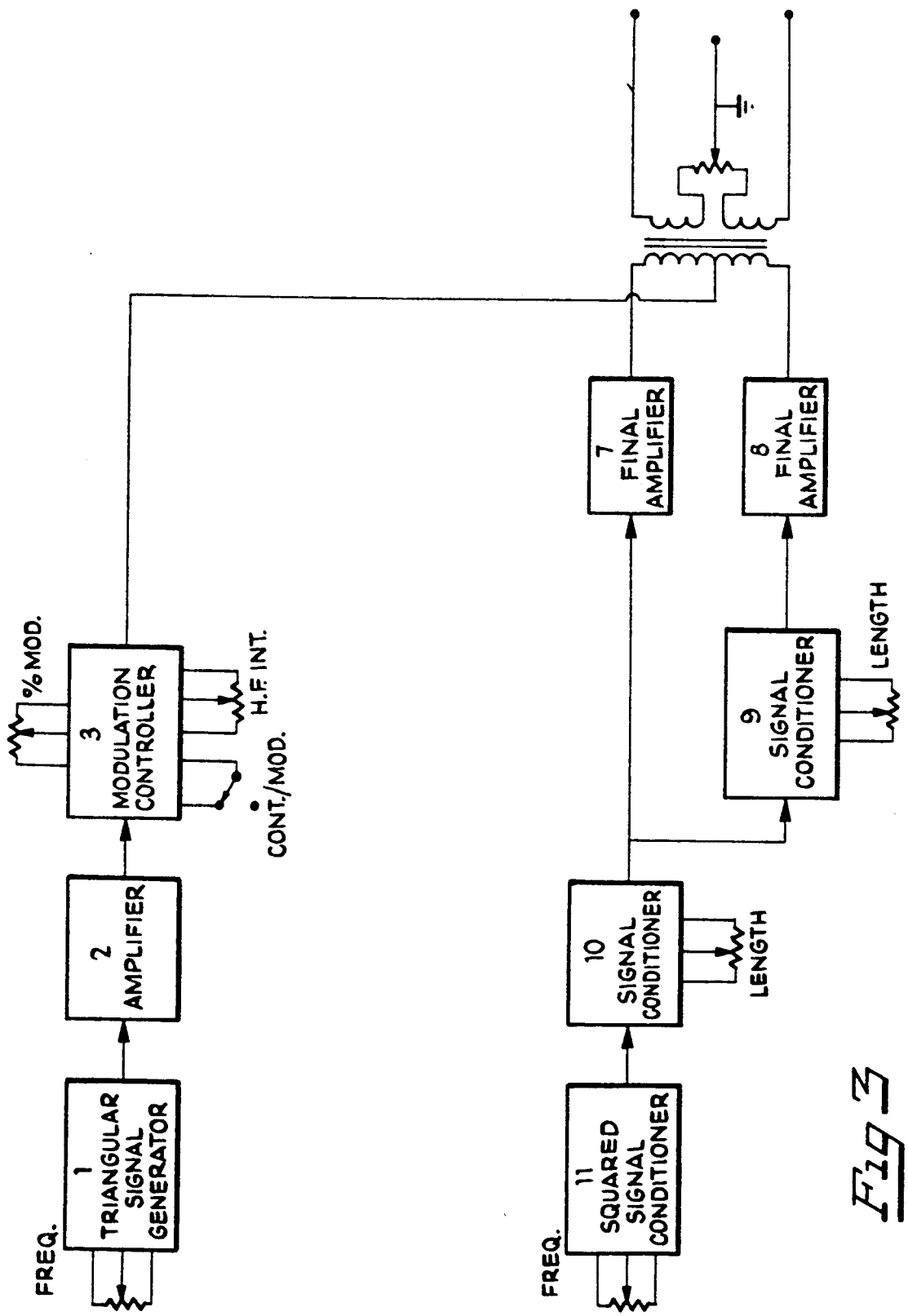
Figure 4:
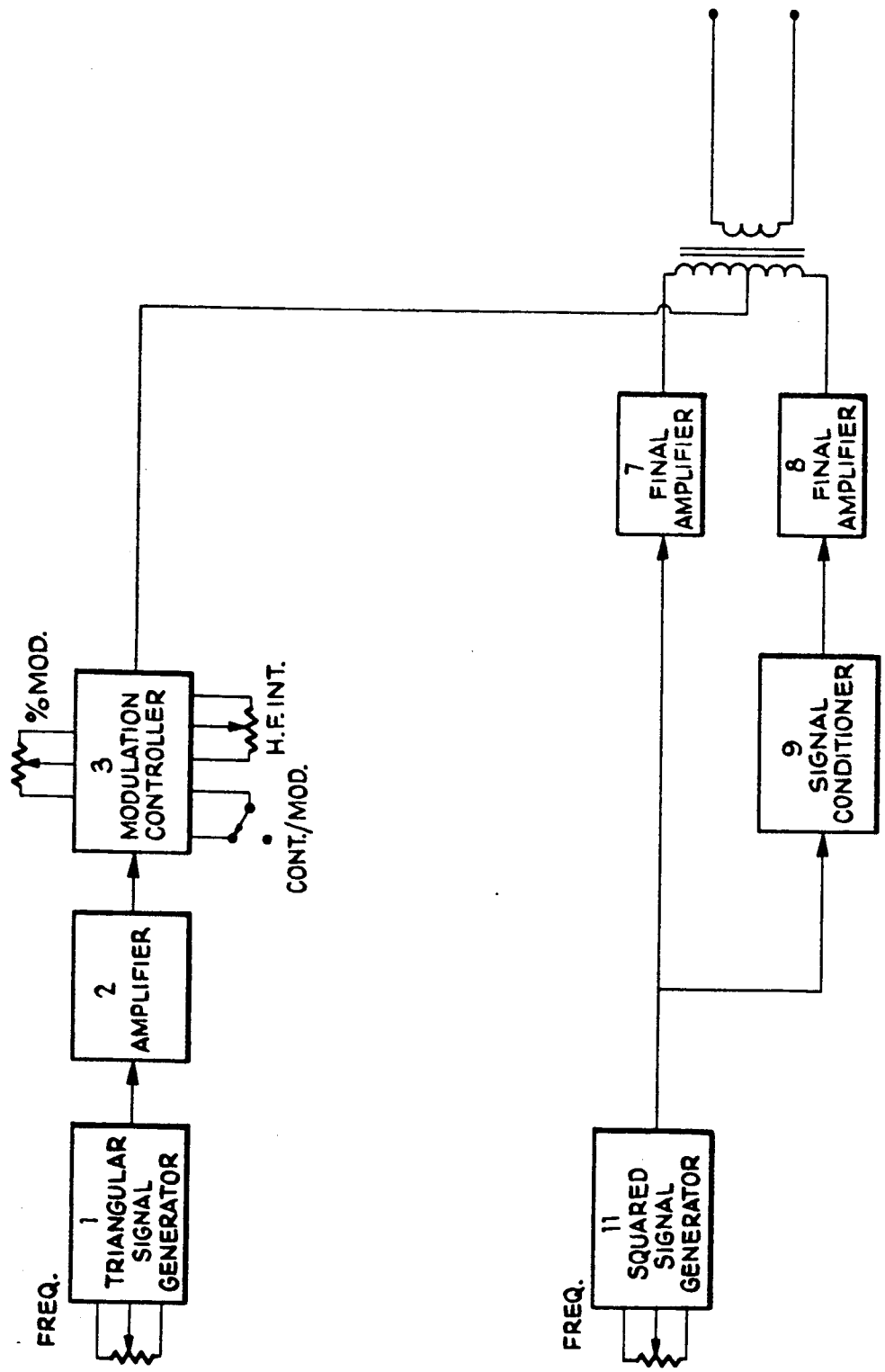

In FIG. 1 where the constitution of the device is shown for odontological application, including the basic units of all the others shown in FIGS. 2, 3 and 4, it may be observed that the electrostimulating device includes a triangular signal generator (1), followed by the amplifier (2), which is connected to the modulation controller (3). A squared signal generator (11) which may also generate other wave forms, according to therapeutic needs, is connected to a 1st stage signal conditioner (10), which, in its turn, is connected in parallel to a frequency divider (6), to a final amplifier (7) and to another 2nd stage signal conditioner (9), and another final amplifier (8) follows the latter. The referred divider (6) is still connected through a key of three positions (A, B, C) to a 3rd stage signal conditioner (5) and this one to a low frequency signal controller (4). This device presents the following characteristics:

Main applications: relaxation, and unprogramming of the chewing and facial muscles, mandibular monitoring and other electrotherapy applications in the facial region.

Technical functions: continuous high frequency (100 Hz), modulated high frequency (0.666 Hz modulation), low frequency (40 ppm, 100 ppm, 300 ppm), continuous high frequency juxtaposed by the low frequency, and modulated high frequency juxtaposed by the low frequency. The three positions (A, B and C) of the frequency divider 6 correspond to the low frequency settings of 40, 100, and 300 ppm, respectively.

Control: high frequency intensity, low frequency intensity, equilibrium, low frequency selector, continuous/modulated high frequency selector, and turn-on/turn-off.

Outputs: two active poles, right and left, and a diffusing pole.

In FIG. 2, the block diagram of a variant of the device is shown, which, as an example of others, presents a basic structure similar to that of FIG. 1, with signal generators (1 and 11), amplifiers (2, 7 and 8), controllers (3 and 4) and conditioners (5, 9 and 10), the main difference being the substitution of the divider (6) by a divider (6') having characteristics different from those of FIG. 1. The referred device has as main characteristics the following:

Main applications: analgesia, muscular stimulation, cicatricial process activation, and general electrotherapy.

Technical functions: continuous high frequency (100 Hz), modulated high frequency (0.666 Hz modulation), low frequency (80 ppm, 160 ppm, 300 ppm), continuous high frequency juxtaposed by the low frequency, and modulated high frequency juxtaposed by the low frequency. The three positions (A, B and C) of the frequency divider 6' correspond to the low frequency settings of 40, 100 and 300 ppm, respectively.

Controls: high frequency intensity, low frequency intensity, continuous/modulated high frequency selector, and turn-on/turn-off low frequency selector.

Outputs: two or more positive poles, and two or more negative poles.

FIG. 3 shows the diagram of another variant of the device and its structure which is generated by the suppression of the low frequency controller (4), of the 3rd stage signal conditioner (S) and of the divider (6), being still possible the suppression of the 1st and 2nd stage signal conditioners (10 and 9).

This variant presents the following characteristics:

Main applications: relaxation, analgesia, lymphatic drainage, and cellular revitalization.

Technical functions: continuous high frequency (100 Hz), and modulated high frequency (modulation with 0.666 Hz) where the low frequency modulation may also be added.

Controls: intensity, equilibrium, continuous/modulated, and turn-on/turn-off high frequency selector.

Outputs: two active poles, right and left, and a diffusing pole.

FIG. 4 is a diagram of the functional structure of another version of the device, having features similar to those of the device in FIG. 3. However, the 1st and 2nd stage signal conditioners (9 and 10) are suppressed and an inverter (12) introduced in their place, is connected to the final amplifier (8). Its main characteristics are:

Applications: analgesia, relaxation, and stimulation.

Technical functions: continuous high frequency (100 Hz), and modulated high frequency (0.666 Hz modulation).

Controls: continuous/modulated high frequency selector.

Outputs: two poles, a positive and a negative one.

This device may also present a model with low frequency modulation.

Figure 5:
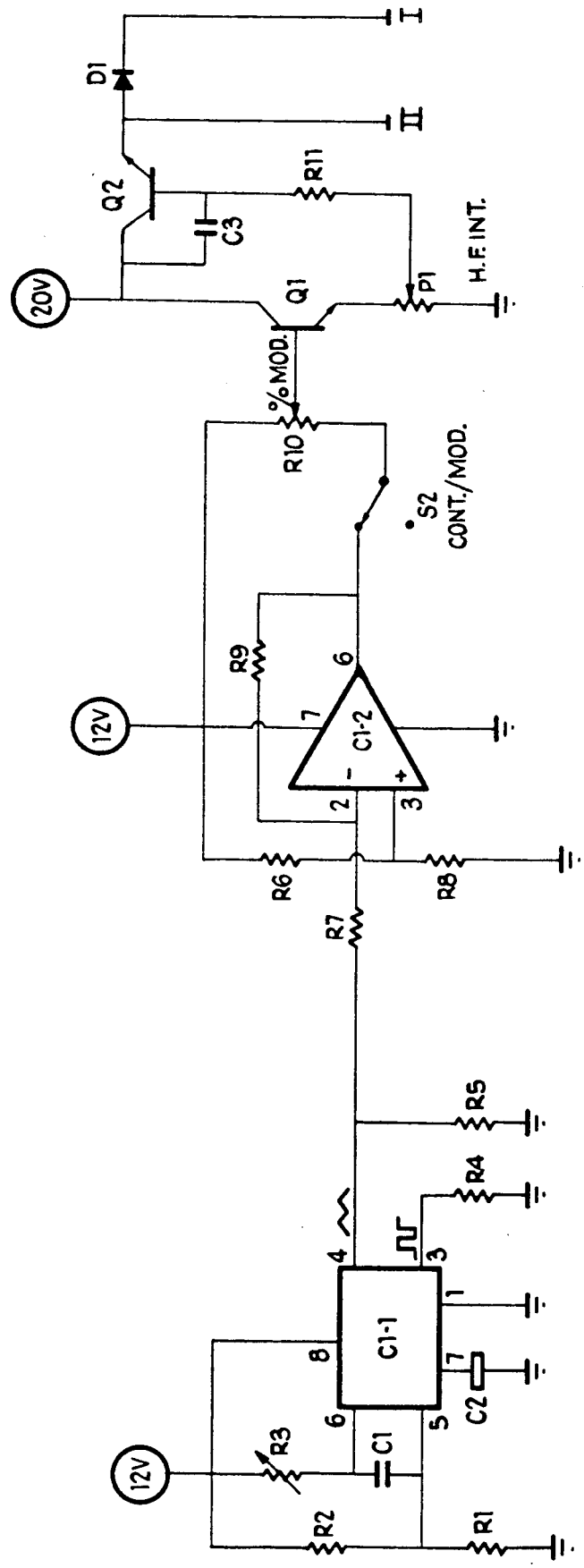
FIG. 5 is a schematic diagram of the basic circuit of the triangular signal generator unit, amplifying unit, modulation control unit and measuring unit.
Figure 6:
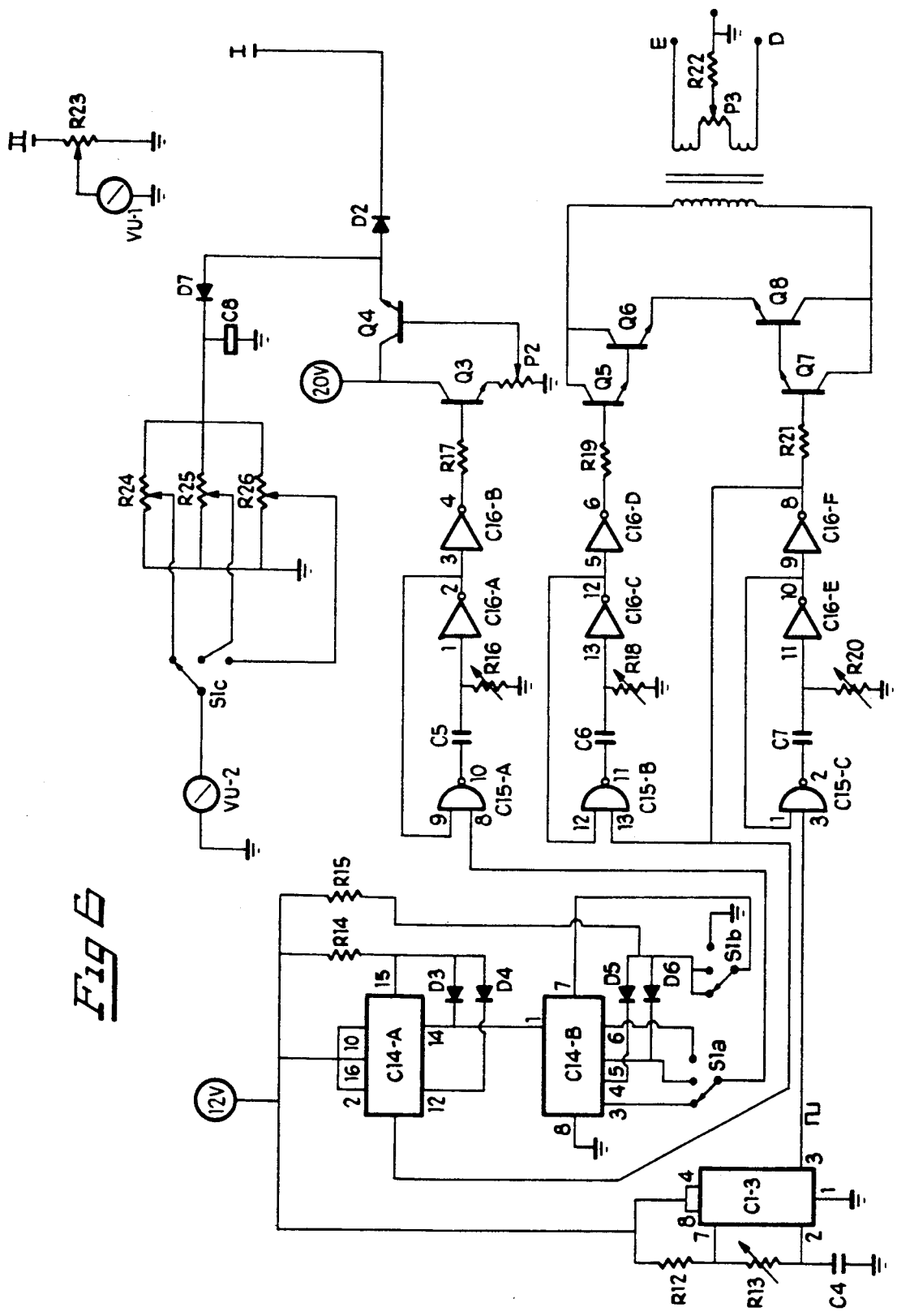
FIG. 6 is a schematic diagram of the basic circuit of the squared signal generator unit, 1st stage signal conditioner, unit, dividing unit, 2nd stage signal conditioner unit, 3rd stage signal conditioner unit, low frequency signal controller unit, final amplification unit and output transformer unit.

FIGS. 5 and 6 together form the general basic circuit of the electrostimulating device of the invention, according to FIG. 1. FIG. 5 shows that the device includes a generating unit of triangular signal in which the high frequency modulation is of the "modulation by amplitude" type, with modulation frequency of 0.666 Hz and of the triangular or sinusoidal type. This unit contains an oscillator which consists of a CI-1 circuit and other circuit supports, which is controlled by tension and with triangular (pin 4) and squared (pin 3) output wave. The adjustment of the frequency is achieved by R3 and C2. From the CI-1 output, only the triangular signal (pin 4) is utilized for the feeding of the operational amplifier CI-2 of the inverter type with an approximate tenfold gain. The referred operational amplifier CI-2 varies the base polarity of the Q1 transistor of the modulation controller, by a variable resistor R10. In the controller, the low frequency is controlled by means of variations in P1, R11 and Q2, associated to variations in Q1. These variations are timed with the above-mentioned frequency of the oscillator, thus obtaining the triangular or sinusoidal modulation of the high frequency signal, the control of the modulation being obtained by tile variable resistor R10. A key S2 acts to selectively impose the modulation. When it is in the turned off position, the base of the Q1 transistor becomes positively polarized, allowing it to conduct the current. In this form, the high frequency intensity may be adjusted by means of P1.

The visual control of the output signal (relative control) in Q2 and Q4 is carried out by instruments of the "VU" type, and the reading of the bottom of the scale is adjusted at high frequency by R23 and at low frequency by R24, R25 and R26, being selected by frequency in the S1-C key, the low frequency pulses being controlled by D7 and C8. Consequently, the visualization of the reading of the measuring instrument is greatly improved. This visualization may also be obtained with light emitting diodes (not shown).

FIG. 6 shows the squared signal generator responsible for the high frequency stimuli, which is obtained by an oscillator composed by the integrated circuit CI-3. This circuit, in the represented configuration, supplies an output signal in pin 3 in the form of a squared wave. Resistors R12, R13 and capacitor C4 form the time constant that determine the oscillation frequency. With resistor R13, which is of the variable type, the generator may be adjusted to the desired frequency.

The signal emitted by CI-3 is then sent to the 1st stage signal conditioner, which consists of a monostable circuit, formed by a logic circuit of the "NAND" type—CI5-C circuit—and by two inverter circuits of the "Schmitt Trigger" type—CI6-E and CI6-P, being that in this unit, resistor R20 and capacitor C7 form the time constant that adjust the length of the pulse to be obtained at the output of transformer T1.

The referred monostable circuit is sensitive to the descent limit of the squared wave signal.

Pin 8 of the CI6-F circuit feeds a final amplifier (7) with rectangular pulses of length defined by the referred monostable circuit in the established frequency, as well as the second stage signal conditioner (9) and the frequency divider block (6).

The signal of the conditioner stage (10) feeds, as stated above, the 2nd conditioner stage (9) that consists of circuits CI5-B, CI5-C and CI5-D and which output feeds, in turn, a second final amplifier (8).

The referred final amplifiers (7 and 8) are transistorized in "Darlington" configuration (Q7, Q8, Q6 and Q5J), each one connected to one of the prime windings of the output transformer.

The output transformer is fed in its center by a continuous tension, which when added to the two sequential signals of the signal conditioner stages, result in a reversion of the magnetic flow in the transformer, producing by induction in the secondary coils, an alternated signal of positive and negative semicycle lengths proportional to the lengths adjusted in the two monostable circuits. The variation of intensity of the output signal is obtained by the variation of the tension level that feeds the center of the transformer. This effect is achieved by the variation in P1 and in the base polarization of Q2.

The low frequency stimuli are obtained from the output of the 1st stage signal conditioner, circuits CI4-A and CI4-B forming the frequency divider circuits.

In reality, these circuits are synchronous meters of the binary type. The first circuit (CI4-A) is configured to divide by 10 and in the second (CI4-B) circuit the subdivisions by 2, 6 and 15 are selected, which permits the desired frequencies from the original frequency.

These pulses obtained from the divider circuit are selected by key S1-a and sent to the 3rd stage signal conditioner, which configuration is identical to the previous ones (1st and 2nd) and formed by circuits CI5-A, CI6-A and CI6-B. In this conditioning stage, the length of the pulse is adjusted by resistor R16, resulting in the doubling of the length of the pulse when compared to the 1st and 2nd signal conditioner stages.

The output of the 3rd conditioning stage feeds transistor Q3 of the low frequency signal controller (4), which conducts only the low frequency pulses. This transistor Q3 and potentiometer P2 form the potentiometer which commands the polarization of Q4 which, by its turn, controls the tension level that feeds the circuit of the primary winding of the output transformer. As the low frequency pulses are obtained from the high frequency oscillator by means of potentiometers, they are always synchronized with the high frequency.

The developed device also has diodes D1 and D2 to block eventual inverse polarizations of transistors Q2 and Q4.

Thus, the high frequency output juxtaposed by low frequency is obtained and controlled with independent intensity controllers. At the output of the device, an output transformer, of the elevating-tension type, is placed with two independent secondary windings and interconnected by the equilibrium potentiometer P3, which carries out the balancing of the stimuli applied to electrodes G and D, in contraposition to eventual differences of resistance of contact with the human skin.

The above description, as previously mentioned, is related to the basic electrostimulating device, shown in the diagram of blocks of FIG. 1, which permits variations in the form of output signal measurement, in the form of feeding or still in the output stimuli of the alternating type with a semicycle in the form of squared wave and another in exponential form. Time controllers and many other resources may also be introduced in the device.

The functions presented at the output of the electrostimulating device according to the invention are:

Continuous High Frequency: A signal with a double-phase or monophase wave form, as already described, is intensity adjustable from 0 to 100% with a frequency in the order of 100 Hz, which can vary from 50 to 5.000 Hz.

Low Frequency: A double-phase or monophase signal as already described, as already described, is frequency adjustable in a range from 0.333 to 10 HZ (internally) and may be selected by the user in the frequencies of 0.666 Hz (40 ppm), 1.666 Hz (100 ppm) and 5 Hz (300 ppm), such selected adjustments being able to change according to the best utilization convenience. The duration of the low frequency pulse is adjustable according to clinical needs, and the intensity is continuously adjustable from 0 to 100%.

High Frequency with Superposed Low Frequency: In this mode, the device produces a signal as described for continuous high frequency and another as described for low frequency, where adjustments may be made which are independent of intensity, and where the low frequency signal should juxtapose the high frequency signal, and such juxtaposition, must occur synchronized in phase and frequency. This juxtaposition is achieved by the High Frequency modulation, where, in a repetitive and adjustable periodicity, a high frequency alternating signal has its intensity increased.

Conjugation of the Continuous High Frequency, Low Frequency and Modulated High Frequency: According to the characterization of the name itself, the device in this mode consists of a combination of stimuli where the modulated high frequency is juxtaposed by the low frequency, and only the juxtaposition of the High Frequency and the Low Frequency is made in a synchronized form, which does not occur with the modulation signal and the low frequency signal, even if both have the same frequency.

Stimulating devices, generally, utilize the basic circuit components as described herein for odontological applications. The device as shown herein, as well as others types, may be commercialized in more than one model, that is "standard" or "deluxe". The models may differ in their details, with complementary electronic circuits, such as time programmer, current meter, automatic turn-off, etc. All such devices require a source of electric energy, including standard household power and batteries.

I claim:

1. An electrostimulating device comprising:
   an electrical signal generator including means for generating a triangular waveform;

an amplifier coupled to said generator for providing an amplified representation of said waveform;

means, coupled to said amplified representation from said amplifier, for modulating said representation and for providing a modulated form thereof at a first output line;

a second electrical signal generator including means for generating a square wave;

a first signal conditioner, coupled to said square wave generator, for processing said square wave;

a frequency divider, coupled to said processed square wave from said first signal conditioner, for providing a divided representation of said processed square wave;

a second signal conditioner, coupled to said processed square wave from said first signal conditioner, for providing a further conditioner representation of said processed square wave;

a third signal conditioner, coupled to said divided representation from said frequency divider, for providing a processed output;

means, coupled between said first output line and said processed output from said third signal conditioner, for control; and output means, coupled between said processed square wave from said first signal conditioner representation from said second signal conditioner and said first output line for amplification and for providing an output signal.

2. A device as in claim 1 wherein said triangular waveform generating means includes an oscillator and said modulating means includes an amplitude modulator.

3. A device as in claim 1 wherein said amplifier includes an inverting-type operational amplifier having a predetermined gain with an output thereof coupled to said modulating means.

4. A device as in claim 3 with said modulating means including a variable resistive element coupled to said operational amplifier output.

5. A device as in claim 1 with said modulating means including a variable resistive element for varying a parameter of said modulated form of said triangular waveform.

6. A device as in claim 1 wherein said square wave generating means includes an adjustable oscillator.

7. A device as in claim 1 with each said signal conditioner including an adjustable monostable circuit.

8. A device as in claim 7 with each said monostable circuit including selected, interconnected logic circuits and means for generating a pulse of a selected length in response to a selected input signal.

9. A device as in claim 1 wherein said output amplification means includes a Darlington-type solid state amplifier coupled to an output transformer.

10. A device as in claim 1 wherein said output amplification means includes a output transformer and a plurality of Darlington-type amplifiers coupled thereto.

11. A device as in claim 1 wherein said frequency divider includes counter means for subdividing said processed square wave.

12. A device as in claim 11 with said subdividing means including at least one, selectively configured, digital counter.

13. A device as in claim 1 with said control means including low frequency control means for providing an adjustable voltage including means for coupling said voltage to said output amplification means.

14. A device, as in claim 1 including a plurality of selectively coupled reverse voltage limiting diodes.

15. A device as in claim 1 with said output amplification means including an output transformer having a plurality of balancing, interconnected output windings.

16. A device as in claim 1 with said modulating means including means for generating a relatively low frequency modulating signal with a frequency range of 0.05 to 8.3 Hz.

* * * * *